(12) United States Patent
Xu et al.

(10) Patent No.: US 12,302,931 B2
(45) Date of Patent: May 20, 2025

(54) SOLID BEVERAGE CONTAINING BARLEY LEAVES AND PREPARATION METHOD THEREOF

(71) Applicant: Zhejiang Medicine Co., Ltd. Xinchang Pharmaceutical Factory, Shaoxing (CN)

(72) Inventors: Xinde Xu, Shaoxing (CN); Zuoliang Wang, Shaoxing (CN); Aiqin Liu, Shaoxing (CN); Tian Xie, Shaoxing (CN); Leiming Yu, Shaoxing (CN); Guozhi Hou, Shaoxing (CN); Qiming Sun, Shaoxing (CN); Yongsheng Shi, Shaoxing (CN)

(73) Assignee: Zhejiang Medicine Co., Ltd. Xinchang Pharmaceutical Factory, Shaoxing (CN)

( * ) Notice: Subject to any disclaimer, the term of this patent is extended or adjusted under 35 U.S.C. 154(b) by 80 days.

(21) Appl. No.: 17/425,346

(22) PCT Filed: Jan. 22, 2020

(86) PCT No.: PCT/CN2020/073747
§ 371 (c)(1),
(2) Date: Jul. 23, 2021

(87) PCT Pub. No.: WO2020/151739
PCT Pub. Date: Jul. 30, 2020

(65) Prior Publication Data
US 2022/0095650 A1 Mar. 31, 2022

(30) Foreign Application Priority Data
Jan. 24, 2019 (CN) .......................... 201910070862.4

(51) Int. Cl.
| | |
|---|---|
| A23L 2/39 | (2006.01) |
| A23L 2/52 | (2006.01) |
| A23L 33/105 | (2016.01) |
| A23L 33/125 | (2016.01) |
| A23L 33/22 | (2016.01) |
| A23P 10/20 | (2016.01) |

(52) U.S. Cl.
CPC .................. *A23L 2/39* (2013.01); *A23L 2/52* (2013.01); *A23L 33/105* (2016.08); *A23L 33/125* (2016.08); *A23L 33/22* (2016.08); *A23P 10/20* (2016.08); *A23V 2002/00* (2013.01)

(58) Field of Classification Search
CPC .......... A23V 2250/214; A23V 2200/15; A23V 2250/21; A23L 2/52; A23L 33/105; A23L 27/88; A23L 2/38; A23L 2/60; A23L 2/56; A23L 33/125; A23L 33/21; A23L 2/39; A23L 29/30; A23L 2/00
See application file for complete search history.

(56) References Cited

FOREIGN PATENT DOCUMENTS

JP 2008006313 A * 1/2008 ............... B01J 2/16

OTHER PUBLICATIONS

Ogasawara Y, JP2008006313-A, Machine Translation English, Jan. 17, 2008, pp. 1-7 (Year: 2008).*

* cited by examiner

*Primary Examiner* — Hong T Yoo
(74) *Attorney, Agent, or Firm* — Ashok Tankha

(57) ABSTRACT

The present invention provides a solid beverage containing barley leaves, comprising the following components: 15-60 wt. % of a barley leaf micro-powder, 10-50 wt. % of xylitol granules, 5-20 wt. % of a matcha powder, 1-10 wt. % of inulin, 0.5-4.0 wt. % of a konjac powder, 0.2-3.0 wt. % of silicon dioxide, and 0.1-3.0 wt. % of sucralose. The present invention also relates to a method for preparing the solid beverage, comprising the following steps: mixing a barley leaf micro-powder, inulin, a konjac powder and matcha powder, and then performing wet granulation on same to obtain granulated powders; passing the granulated powders through a 20-mesh sieve after drying same to obtain whole granules; and uniformly mixing the whole granules with xylitol granules, sucralose and silicon dioxide, and then sub-packaging same, so as to obtain the solid beverage. The solid beverage is easy and fast to dissolve, does not separate, and tastes refined and smooth.

2 Claims, No Drawings

SOLID BEVERAGE CONTAINING BARLEY LEAVES AND PREPARATION METHOD THEREOF

CROSS-REFERENCE TO RELATED APPLICATIONS

This application is a national stage application of the Patent Cooperation Treaty (PCT) international application titled "Solid Beverage Containing Barley Leaves And Preparation Method Thereof", international application number PCT/CN2020/073747, filed in the China National Intellectual Property Administration (CNIPA) on Jan. 22, 2020, which claims priority to and the benefit of the patent application titled "Solid Beverage Containing Barley Leaves And Preparation Method Thereof", patent application number 201910070862.4, filed in the China National Intellectual Property Administration (CNIPA) on Jan. 24, 2019. The specifications of the above referenced patent applications are incorporated herein by reference in their entirety.

FIELD OF THE INVENTION

The present invention relates to a solid beverage containing barley leaves and preparation method thereof. The obtained solid beverage has good solubility and taste, and belongs to the field of food processing.

BACKGROUND

Barley leaves are barley seedling that grows to 20-30 cm, rich in natural vitamins, chlorophyll, dietary fiber, active enzymes, minerals and multiple active ingredients, more than 20 kinds of enzymes such as superoxide dismutase, peroxidase, cytochrome oxidase and transhydroxylase, and have effects of reducing blood lipids, reducing blood pressure, reducing blood sugar, anti-oxidation, and improving cell nutrition. Barley leaves can comprehensively enhance physical fitness and improve body immunity so as to achieve the purpose of preventing diseases.

Barley leaf powder is a purely natural food, is an alkaline food, without any harmful side effects. It can strengthen the immune capacity of our normal cells, thereby resisting the production of cancer cells, and effectively blocking the transformation and deterioration of cancer cells. In addition, barley leaf powder is also rich dietary fiber and can control the increase of blood sugar after a meal, and reduce the burden on pancreas, and it is a good food for diabetics patients and hyperlipidemia patients. At the same time, it has good improvement effects on regulating gastrointestinal function because barley leaf powder contains a lot of dietary fiber.

Barley leaf powder in the prior art is mainly obtained by planting barley seedlings in the field, harvesting the aerial parts when the barley seedlings growing 20-30 cm high, and after washing, drying by air or drying by stoving, crushing and sieving; or after washing, spin-drying, wet crushing extraction, filtration, filtrate concentration, spray drying so as to obtain barley leaf juice powder.

Due to barley leaf powder having good physiological functions, there are more barley leaf powder or barley leaf juice powder solid beverages in the market.

CN 106879902 A provides a barley seedling powder solid beverage. Besides barley seedling powder, it also includes kelp powder, broccoli powder, mushroom powder, lemon fruit powder, vegetable protein and animal protein etc. The taste of solid drinks is poor with a bitter taste when eating. Some flavoring agents have to be added, and juice or dairy products are also added when adjusting in order to overcome these unfavorable tastes.

CN 105077029A relates to a zinc-rich barley seedling dinner meal substitute powder and preparation method thereof. The formula contains a lot of mushroom enzyme powders, fruit enzyme powders, rice powders, cooked nuts, etc. Barley seedling powders occupy less quantity because it is a meal substitute powder, and the cultivation of zinc-rich barley seedlings is more troublesome.

CN 101214079 A discloses is a barley tender seedling solid beverage and its production process, comprising barley tender seedling powders, barley malt powders, spirulina, xanthan gum, sucrose esters, sodium alginate, sodium carboxymethyl cellulose, and amorphous silica, etc. The formula and process are very complicated such as using more food additives including emulsifiers and stabilizer in order to solve the problem of fine taste and blendability of products. But the effect is not particularly good.

CN 107279743 A describes a barley leaf green juice powder and its preparation method. The barley leaf and kiwi pulp are squeezed at low temperature, adding stabilizer, homogenizing process, drying in vacuum, crushing, jet pulverizing, etc., and finally obtain green juice powders. In this process, using a high-energy-consuming vacuum freeze-drying process, and crushing final green juice powders to 1000-1600 mesh powders. But it consumes a lot of energy and tends to agglomerate when dissolved.

In general, there are many solid beverages containing barley leaf powders (also called "barley seedling powders", "barley tender seedling powders", "barley green juice powders", etc.) as main raw materials. But common existing problems in these solid beverage formulas or processes are: with no good taste, rough taste and not delicate, strong grassy smell (grass smell); or poor flushing, easily caking when brewing, and easily precipitating and stratifying quickly after mixing. Consumer experience is poor. Moreover, the taste of these solid drinks is often at odds with their tonality. The particle size of barley leaf powders is required to be as small as possible, and the particle size is usually required to be about 10 microns in order to make the solid beverage taste more fine. And the fine particle size is not good for flushing of solid beverages and easily agglomerating and bonding during brewing. And the requirements for crushing and energy consumption are very high to achieve such a small particle size. Although the coarse particle size is good for dispersion during brewing, it is easy to delaminate and taste bad when the beverage is standing, and the taste is not good.

In the prior art, it is generally adding other fruit juice powder or flavoring agents in order to solve the problem of grassy taste in the taste of barley powder solid beverages, and at the same time overcome the defect of rough taste by reducing the fineness of barley grass powder. It is required that the particle size of barley leaf powders is about 10 microns (1250 mesh) to eliminate the roughness in the oral cavity. However, on the one hand, it takes a lot of energy to achieve that size if the particle size of barley leaf powders is as small as 10 microns; on the other hand, it is easy to agglomerate due to surface tension when dissolving and brewing, and it is also easy to stick to the stirring rod and the cup wall when stirring, causing inconvenience for drinking.

It is very necessary to develop a solid beverage containing barley leaf powders It can simultaneously meet the two conditions of having a good taste especially no roughness, and good brewing performance, so that consumers have a good consumption experience. The present invention is researched and developed based on this purpose.

SUMMARY OF THE INVENTION

The present invention provides a solid beverage containing barley leaves and preparation method thereof. Solid beverages also contain inulin and konjac powder to be beneficial to intestinal health besides barley leaf powders. Firstly partial components in the solid beverage formula are pre-mixed and granulated, and then mixed with other components to form the final product in order to overcome defects such as a roughness feeling in the mouth after the solid beverage brewed, and easily agglomerating and sticking on the wall during preparation. The solid beverage product obtained by the present invention is easy to prepare and dissolves quickly, does not stratify, and has a fine and smooth mouthfeel, and has a good sense of consumer experience.

In order to overcome the shortcomings of the prior art, the present invention provides a solid beverage containing barley leaves and a process thereof, wherein adding a certain amount of inulin and konjac powders, and then granulating, to obtain solid beverage with easily brew. The solid beverage does not agglomerate and stick to walls, and does not easy to stratify after brewing, has a good taste, fine and no grassy smell.

According to one aspect of the present invention, the present invention provides a solid beverage containing barley leaves. The solid beverage comprises the following components: 15-60 wt. % of barley leaf micro-powders, 10-50 wt. % of xylitol granules, 5-20 wt. % of matcha powders, 1-10 wt. % of inulin, 0.5-4.0 wt. % of konjac powders, 0.2-3.0 wt. % of silicon dioxide, and 0.1-3.0 wt. % of sucralose.

According to one aspect of the present invention, the present invention provides a method of preparing for a solid beverage containing barley leaves. The method includes the following steps: method of preparing for a solid beverage containing barley leaves, comprising the following steps: a) mixing a barley leaf micro-powder, inulin, konjac powder and matcha powder and then wet granulating to obtain granulated powders; b) drying the granulated powders of step a) and passing through a 20-mesh sieve to obtain a whole granule; and c) uniformly mixing the whole granule of step b) with xylitol particles, sucralose and silicon dioxide, and then packaging them to obtain a solid beverage. Preferably, the particle size of the barley leaf micro-powders is 15-50 microns.

Inulin is a reserve polysaccharide in plants. It is a natural water-soluble dietary fiber. It is almost undigested and undigested by gastric acid. It is only beneficial microbes used in the colon to improve the intestinal environment. It has the function of regulating intestinal microflora, improving intestinal health and preventing constipation, and further it has the function of controlling blood lipids, lower blood sugar, and promote mineral absorption. At the same time, it can significantly reduce the roughness feeling caused by barley micro-powders when using with xylitol because inulin is rich in fructose and has a refreshing taste. The particle size of inulin on the market is generally between 70-420 microns.

Konjac powder is also known as "konjac micro-powder", "purified konjac powder", "purified konjac micro-powder", etc. It has the effects of reducing fat, reducing blood sugar, preventing cancer, and laxative. The glucomannan contained in konjac powder is a high-molecular compound with strong water absorption. The volume can expand 80-100 times after absorbing water. It is not easy to be digested and absorbed after eating. It can absorb cholesterol and bile acids. It has a certain effects in reducing blood pressure and reducing cardiovascular disease. Konjac powder (its particle size is generally less than 125 microns) is easy to granulate, has a large viscosity after dissolution, and has good aqueous solution stability and is not easy to layer. In addition, it also has a lubricating and refreshing feeling. These can improve the stability and taste of water dispersion of barley leaf powder.

Matcha tea is the freshest and most nutritious tea so far. It enhances consumption desire because of its natural bright green color, and it is very popular among consumers because of its natural fragrance. The particle size of matcha powders on the market is generally between 80-250 microns.

The wet granulation is carried out by conventional methods after mixing barley powders, inulin, konjac powders and matcha powders. The wetting agent for the wet granulation is aqueous ethanol, and the binder is konjac powders, methyl cellulose, sodium carboxymethyl cellulose, low-substituted hydroxypropyl cellulose, hydroxypropyl methyl cellulose, or polyvinylpyrrolidone (PVP), etc. It is worth noting that part of konjac powders, methyl cellulose, sodium carboxymethyl cellulose, low-substituted hydroxypropyl cellulose, hydroxypropyl methyl cellulose, or polyvinylpyrrolidone (PVP) can be dissolved in aqueous ethanol as an adhesive, in order to prevent or reduce the effect of the introduction of a small amount of binders on the taste of the solid drink of the final product solid beverage. The concentration of the binder is between 1-15 wt. %.

Dry the above-mentioned materials wet-granulated, and then sieve the whole grain through 20 mesh, and uniformly mix with granular xylitol, sucralose and silicon dioxide, and then subpackage and obtain solid beverage products. The entire operation is carried out in a Class D clean area to prevent from microbial contamination.

The advantages of the method of the present invention are as follows. The method can effectively eliminate the roughness feeling and grassy smell of barley powders, and has a delicate, smooth and fragrant feeling by using inulin, xylitol, matcha powders, and konjac powders in a certain amount, adding sucralose makes the solid beverage solution moderate sweetness and has a good taste. In addition, pre-wet granulating barley leaf micro-powders, inulin, konjac powders and then mixing with granular xylitol, sucralose and silicon dioxide can ensure that the final solid beverage product has good dissolution performance, and dissolves and disperses quickly, and dissolves without clumping and sticking to walls. Furthermore, the addition of inulin and konjac powder increases the viscosity of the solution after they are dissolved, and has certain solution stabilizing effects, so that the dissolved and dispersed beverage is not easy to layer due to sedimentation. Therefore, the solid beverage of the present invention is easy to brew, does not clump and stick to the wall, is not easy to layer after brewing, has a good mouthfeel, delicate and without grassy smell. These advantages make the final solid beverage product of the present invention have a good consumption experience. All materials of the present invention are conventional materials that can be purchased in the market.

DETAILED DESCRIPTION OF THE INVENTION

Hereinafter, the present invention will be further described with reference to the embodiments. The embodiments of the present invention are only used to illustrate the technical solutions of the present invention, and do not limit the present invention.

Example 1

A solid beverage containing barley leaf particles, the solid beverage comprising the following components:

| | |
|---|---|
| Barley leaf micro-powders: | 60% |
| Xylitol: | 10% |
| Matcha powders: | 15% |
| Inulin: | 5% |
| Konjac powders: | 4% |
| Silicon dioxide: | 3% |
| Sucralose: | 3% |
| Total amount: | 100% (the ingredients: 3.0 kg). |

Process of Preparation: Uniformly mix barley leaf micro-powders (the particle size: 15 microns), matcha powders (commercially available particle size: 80-250 microns), inulin (commercially available particle size: 70-420 microns) and part of konjac powders (0.07 kg, commercially available the particle size: less than 125 microns) together. In addition, dissolve 0.05 kg of konjac powders in 500 g of 75% ethanol as a binder solution for wet granulation. After wet granulation, dry, and then sieve through a 20-mesh sieve; food grade) to obtain a whole grain. And then uniformly mix the whole grain with silicon dioxide (commercially available food grade) and sucralose (commercially available food grade), to obtain a solid beverage after sub-packaging. The entire operation is operated in a Class D clean area.

The solid beverage obtained by the present invention has good brewing properties, no agglomeration, no sticking to the wall, no rapid layering, very fine and smooth mouthfeel, no adverse afterfeeling, has natural fragrance and good experience. The brewing performance and taste evaluation of this solid beverage are shown in Table 1.

Example 2

A solid beverage containing barley leaf particles, the solid beverage comprising the following components:

| | |
|---|---|
| Barley leaf micro-powders: | 15% |
| Xylitol: | 50% |
| Matcha powders: | 20% |
| Inulin: | 10% |
| Konjac powders: | 1.9% |
| Silicon dioxide: | 1.5% |
| Sucralose: | 1.5% |
| sodium carboxy methyl cellulose | 0.1% |
| Total amount: | 100% (the ingredients: 3.0 kg). |

Process of Preparation: Uniformly mix barley leaf powders (the particle size: 50 microns), matcha powder (commercially available particle size: 80-250 microns), inulin (commercially available particle size: 70-420 microns), konjac powder (commercially available particle size: less than 125 Micron) together. In addition, dissolve 0.03 kg sodium carboxymethyl cellulose in 3000 g 75% ethanol as a binder solution for wet granulation. After wet granulation, dry, and then sieve through a 20-mesh sieve; food grade) to obtain a whole grain. And then uniformly mix the whole grain with granular xylitol (commercially available food grade), silicon dioxide (commercially available food grade), and sucralose (commercially available food grade) to obtain a solid beverage after sub-packaging. The entire operation is operated in a Class D clean area.

The solid beverage obtained by the present invention has good brewing properties, no agglomeration, no sticking to the wall, no rapid layering, full on the palate, no adverse afterfeeling, has natural fragrance and good experience. The brewing performance and taste evaluation of this solid beverage are shown in Table 1.

Example 3

A solid beverage containing barley leaf particles, the solid beverage comprising the following components:

| | |
|---|---|
| Barley leaf micro-powders: | 45% |
| Xylitol: | 38% |
| Matcha powders: | 5% |
| Inulin: | 1% |
| Konjac powders: | 4% |
| Silicon dioxide: | 3% |
| Sucralose: | 3% |
| Polyvinylpyrrolidone(PVP) | 1% |
| Total amount: | 100% (the ingredients: 5.0 kg). |

Process of Preparation: Uniformly mix barley leaf powders (the particle size: 25 microns), matcha powders (commercially available particle size: 80-250 microns), inulin (commercially available particle size: 70-420 microns), and konjac powders (commercially available particle size: less than 125 Micron) together. In addition, dissolve 0.5 kg polyvinylpyrrolidone (PVP) in 2800 g 75% ethanol as a binder solution for wet granulation. After wet granulation, dry, and then sieve through a 20-mesh sieve; food grade) to obtain a whole grain. And then uniformly mix the whole grain with granular xylitol (commercially available food grade), silicon dioxide (commercially available food grade), and sucralose (commercially available food grade) to obtain a solid beverage after sub-packaging. The entire operation is operated in a Class D clean area.

The solid beverage obtained by the present invention has good brewing properties, no agglomeration, no sticking to the wall, no rapid layering, full on the palate, no adverse afterfeeling, has natural fragrance and good experience. The brewing performance and taste evaluation of this solid beverage are shown in Table 1.

Example 4

A solid beverage containing barley leaf particles, the solid beverage comprising the following components:

| | |
|---|---|
| Barley leaf micro-powders: | 40% |
| Xylitol: | 35% |
| Matcha powders: | 14% |
| Inulin: | 9.2% |
| Konjac powders: | 0.5% |

-continued

| | |
|---|---|
| Silicon dioxide: | 0.2% |
| Sucralose: | 0.1% |
| Methyl cellulose | 1% |
| Total amount: | 100% (the ingredients: 5.0 kg). |

Process of Preparation: Uniformly mix barley leaf powders (particle size: 35 microns), matcha powders (commercially available particle size: 80-250 microns), inulin (commercially available particle size: 70-420 microns), konjac powders (commercially available particle size: less than 125 Micron) together. In addition, dissolve 0.5 kg methyl cellulose in 3300 g 70% ethanol as a binder solution for wet granulation. After wet granulation, dry and then sieve through a 20-mesh sieve; food grade) to obtain a whole grain. And then uniformly mix the whole grain with granular xylitol (commercially available food grade)), silicon dioxide (commercially available food grade), and sucralose (commercially available food grade) to obtain a solid beverage after sub-packaging. The entire operation is operated in a Class D clean area.

The solid beverage obtained by the present invention has good brewing properties, no agglomeration, no sticking to the wall, no rapid layering, full on the palate, no adverse afterfeeling, has natural fragrance and good experience. The brewing performance and taste evaluation of this solid beverage are shown in Table 1.

Example 5

A solid beverage containing barley leaf particles, the solid beverage comprising the following components:

| | |
|---|---|
| Barley leaf micro-powders: | 32% |
| Xylitol: | 35% |
| Matcha powders: | 18.7% |
| Inulin: | 7.5% |
| Konjac powders: | 3.6% |
| Silicon dioxide: | 1.2% |
| Sucralose: | 1.0% |
| Hydroxypropyl methyl cellulose | 1.0% |
| Total amount: | 100% (the ingredients: 3.0 kg). |

Process of Preparation: Uniformly mix barley leaf powders (the particle size: 45 microns), matcha powders (commercially available particle size: 80-250 microns), inulin (commercially available particle size: 70-420 microns), konjac powders (commercially available particle size: less than 125 Micron) together. In addition, dissolve 0.03 kg of hydroxypropyl methylcellulose in 600 g of 50% ethanol as a binder solution for wet granulation. After wet granulation, dry and then sieve through a 20-mesh sieve; food grade) to obtain a whole grain. And then uniformly mix the whole grain with granular xylitol (commercially available food grade), silicon dioxide (commercially available food grade), and sucralose (commercially available food grade) to obtain a solid beverage after sub-packaging. The entire operation is operated in a Class D clean area.

The solid beverage obtained by the present invention has good brewing properties, no agglomeration, no sticking to the wall, no rapid layering, full on the palate, no adverse afterfeeling, has natural fragrance and good experience. The brewing performance and taste evaluation of this solid beverage are shown in Table 1.

Example 6

A solid beverage containing barley leaf particles, the solid beverage comprising the following components:

| | |
|---|---|
| Barley leaf micro-powders: | 40% |
| Xylitol: | 36% |
| Matcha powders: | 12% |
| Inulin: | 5.6% |
| Konjac powders: | 2.4% |
| Silicon dioxide: | 1.5% |
| Sucralose: | 1.5% |
| low-substituted hydroxypropyl cellulose: | 1.0% |
| Total amount: | 100% (the ingredients: 3.0 kg). |

Process of Preparation: Uniformly mix barley grass powder (the particle size: 15 microns), matcha powder (commercially available particle size: 80-250 microns), inulin (commercially available particle size: 70-420 microns), konjac powder (commercially available particle size: less than 125 Micron) together. In addition, dissolve 0.03 kg low-substituted hydroxypropyl cellulose (produced by Huzhou Zhanwang Pharmaceutical Co., Ltd., model number: LH21) in 300 g 30% ethanol as a binder solution for wet granulation. After wet granulation, dry and then sieve through a 20-mesh sieve; food grade) to obtain a whole grain. And then uniformly mix the whole grain with granular xylitol (commercially available food grade), silicon dioxide (commercially available food grade), and sucralose (commercially available food grade) to obtain a solid beverage after sub-packaging. The entire operation is operated in a Class D clean area.

The solid beverage obtained by the present invention has good brewing properties, no agglomeration, no sticking to the wall, no rapid layering, full on the palate, no adverse afterfeeling, has natural fragrance and good experience. The brewing performance and taste evaluation of this solid beverage are shown in Table 1.

Comparative Example 7

A solid beverage containing barley leaf powders, the solid beverage comprising the following components:

| | |
|---|---|
| Barley leaf micro-powders: | 32% (the particle size: 50 microns) |
| Barley malt powders: | 15.0% |
| Spirulina: | 28.0% |
| Xanthan Gum: | 9.5% |
| Sucrose ester: | 4.5% |
| Sodium Alginate: | 4.0% |
| Sodium carboxymethyl cellulose: | 5.0% |
| Amorphous silicon dioxide: | 2.0% |
| Total amount: | 100% (the ingredients: 3.0 kg). |

Various of auxiliary materials are commercially available. The process is to directly mix the main materials with auxiliary materials and then package them according to the prior art. The product obtained is easy to layer, has a strong grassy taste, and has a poor taste. The brewing performance and taste evaluation of this solid beverage are shown in Table 1.

Comparative Example 8

A solid beverage containing barley leaf powders, the solid beverage comprising the following components:

| | |
|---|---|
| Barley leaf micro-powders: | 50% (sieving in a 1250 mesh, the particle size: 10 microns) |
| Xylitol: | 20% |
| Matcha powders: | 12% |
| Inulin: | 7% |
| Konjac powders: | 4% |
| Silicon dioxide: | 3% |
| Sucralose: | 4% |
| Total amount: | 100% (the ingredients: 3.0 kg). |

Various of auxiliary materials are commercially available. The process is to directly mix the main materials with auxiliary materials and then package them according to the prior art. The product obtained is easy to agglomerate when being dissolved, and is not easy to disperse. It is left for 2 hours to layer after dissolving. The brewing performance and taste evaluation of this solid beverage are shown in Table 1.

TABLE 1

Evaluation of solubility and taste of each product

| Sample | Dispersion | Whether layered | Taste | Smell |
|---|---|---|---|---|
| Example 1 | completedly dispersion within 25 seconds | without being layered for 48 hrs | delicate and smooth | special matcha fragrance |
| Example 2 | completedly dispersion within 15 seconds | without being layered for 36 hrs | delicate and smooth | special matcha fragrance |
| Example 3 | completedly dispersion within 25 seconds | without being layered for 48 hrs | delicate and smooth | Very pleasant fragrance |
| Example 4 | completedly dispersion within 30 seconds | without being layered for 30 hrs | delicate and smooth | special matcha fragrance |
| Example 5 | completedly dispersion within 25 seconds | without being layered for 48 hrs | delicate and smooth | special matcha fragrance |
| Example 6 | completedly dispersion within 30 seconds | without being layered for 48 hrs | delicate and smooth | special matcha fragrance |
| Example 7 | completedly dispersion within 25 seconds | layered at once after setting | rough uncomfortable feeling | grassy smell |
| Example 8 | agglomerated and sticked to the wall during dispersion, and not easily dispersed | incomplete dissolution | fine but not lubricated | matcha flavor |

The present invention illustrates by the above examples, however, it is understood that, the present invention is not limited to special instance and implementation scheme described herein. Here the purpose including these special instances and implementation schemes is aimed at helping the persons skilled in the art to achieve this invention. It is easy for any persons skilled in the art to carry out further improvement and perfection not from the spirit and scope of the invention, so the present invention is just limited by the content and scope of claims of the present invention, its intention to cover all included all alternative solutions and equivalent solutions within the spirit and scope of the present invention limited by the appendix claims.

We claim:

1. A solid beverage containing barley leaves, the solid beverage prepared by:
    (a) mixing barley leaf micro-powder, inulin, konjac powder and matcha powder and then wet granulating to obtain a granulated powder;
    (b) drying the granulated powders of step (a) and passing through a 20-mesh sieve to obtain a whole granule; and
    (c) uniformly mixing the whole granule of step (b) with xylitol granules, sucralose and silicon dioxide, and then packaging them to obtain the solid beverage;
wherein the solid beverage contains:
    15-60 wt. % of the barley leaf micro-powder;
    10-50 wt. % of the xylitol granules;
    5-20 wt. % of the matcha powder;
    1-10 wt. % of the inulin;
    0.5-4.0 wt. % of the konjac powder;
    0.2-3.0 wt. % of the silicon dioxide; and
    0.1-3.0 wt. % of the sucralose.

2. The solid beverage of claim 1, wherein the particle size of the barley leaf micro-powder is 15-50 microns.

* * * * *